United States Patent [19]

Lund et al.

[11] Patent Number: 4,679,570
[45] Date of Patent: Jul. 14, 1987

[54] PHONOCARDIOSCOPE WITH A LIQUID CRYSTAL DISPLAY

[75] Inventors: Walter Lund, Berlin; Lou Berman, Bridgeport, both of Conn.; Felix Dothan, Jerusalem, Israel

[73] Assignee: Phonocardioscope Partners, New Haven, Conn.

[21] Appl. No.: 670,854

[22] Filed: Nov. 13, 1984

[51] Int. Cl.⁴ .............................................. A61B 5/02
[52] U.S. Cl. ................................................ 128/715
[58] Field of Search ............... 128/701, 709, 710, 715, 128/901, 902, 773, 908, 703, 702; 364/413, 415, 417

[56] References Cited

U.S. PATENT DOCUMENTS

| | | | |
|---|---|---|---|
| 3,318,303 | 5/1967 | Hammacher | 128/715 |
| 4,161,945 | 7/1979 | Grossman | 128/901 |
| 4,170,717 | 10/1979 | Walshe | 128/715 |
| 4,220,160 | 9/1980 | Kimball et al. | 128/715 |
| 4,331,756 | 5/1982 | Apple et al. | 128/715 |
| 4,356,475 | 10/1982 | Neumann et al. | 128/709 |
| 4,362,164 | 12/1982 | Little et al. | 128/715 |
| 4,475,558 | 10/1984 | Brock | 128/710 |
| 4,483,346 | 11/1984 | Slavin | 128/710 |

FOREIGN PATENT DOCUMENTS 2929688 2/1981 Fed. Rep. of Germany ...... 128/773

Primary Examiner—William E. Kamm
Attorney, Agent, or Firm—Armstrong, Nikaido, Marmelstein & Kubovcik

[57] ABSTRACT

A phonocardioscope apparatus is provided for monitoring heart functions. The apparatus comprises an acoustical transducer for detecting the sound of heartbeats and producing an analog electrical signal in response thereto. An analog-to-digital converter converts the analog heartbeat signal to a digital heartbeat signal. The transducer may be coupled to the analog-to-digital converter by means of a non-linear amplifier which enhances the signal/noise ratio of the signal. The output of the analog-to-digital converter, which is the digital heartbeat signal, is stored in at least one RAM and the data stored in the RAM is then displayed on the liquid crystal display and may be printed as well. A microprocessor functioning as a CPU controls the operation of the A/D converter, the RAMs and the liquid crystal display. Further, a keyboard is coupled to the apparatus for permitting an operator to select the mode or characteristics of the display.

6 Claims, 2 Drawing Figures

PHONOCARDIOSCOPE WITH A LIQUID CRYSTAL DISPLAY

BACKGROUND OF THE INVENTION

1. Field of the Invention

The present invention is directed to a phonocardioscope and more particularly to a phonocardioscope with a liquid crystal display.

2. Description of the Prior Art

A phonocardioscope is a device for monitoring the activity of a heart. An acoustical transducer detects the sounds of a heartbeat and converts this signal to an electrical signal. The electrical signal is then displayed on a device such as a CRT or a graphic plotting device for the purpose of analysis. There are however, several disadvantages with these prior art devices.

One of the primary disadvantages is the size of prior art phonocardioscopes, specifically these prior art devices are very large. Because of the size and complexity of the device, the device can not be hand held or easily moved around. Rather, the device is large and heavy, and usually requires a cart or some other suitable carrying apparatus. This limits the use of the device to a restricted area such as a hospital or doctor's office.

Another serious disadvantage of prior art phonocardioscopes which use a CRT display, is that the display is constantly changing as a function of time. Thus, the physician can not study and analyze the heartbeat for a particular period of time because the display is constantly changing. In prior art devices which use a graphic recording device, the recording device is complex and expensive, and further, it is less reliable than an electronic type display.

SUMMARY OF THE INVENTION

It is the primary object of the present invention to provide a phonocardioscope with a liquid crystal display, which is small and relatively simple as compared to a prior art CRT display type phonocardioscope.

It is another object of the present invention to provide a phonocardioscope which can be hand held and thus is easily transportable to any location.

It is still another object of the present invention to provide a phonocardioscope which displays a detected heartbeat during a predetermined period of time, the display being maintained for any period of time desired by the user.

It is still another object of the present invention to provide a phonocardioscope in which a heartbeat is acoustically detected and converted to an analog electrical signal. The analog signal is then converted to a digital signal and the digital signal is stored and then displayed on a liquid crystal display device.

It is still a further object of the present invention to provide a phonocardioscope which can provide a user with a printed record of the heartbeat data.

The present invention is directed to a phonocardioscope apparatus for monitoring heart functions. The apparatus comprises an acoustical transducer for detecting the sound of heartbeats and producing an analog electrical signal in response thereto. An analog-to-digital converter converts the analog heartbeat signal to a digital heartbeat signal. The transducer may be coupled to the analog-to-digital converter by means of a non-linear amplifier which enhances the signal/noise ratio of the signal. The output of the analog-to-digital converter, which is the digital heartbeat signal, is stored in at least one RAM and the data stored in the RAM is then displayed on the liquid crystal display. A microprocessor, functioning as a CPU, controls the operation of the A/D converter, the RAMs and the liquid crystal display. Further, a keyboard is coupled to the apparatus for permitting an operator to select the mode or characteristics of the display. Since the sampled data is converted to digital data it becomes very simple to provide a printed or hard copy of the sampled heartbeat using a dot printer, for example.

DETAILED DESCRIPTION OF THE PREFERRED EMBODIMENT

Figure 1:
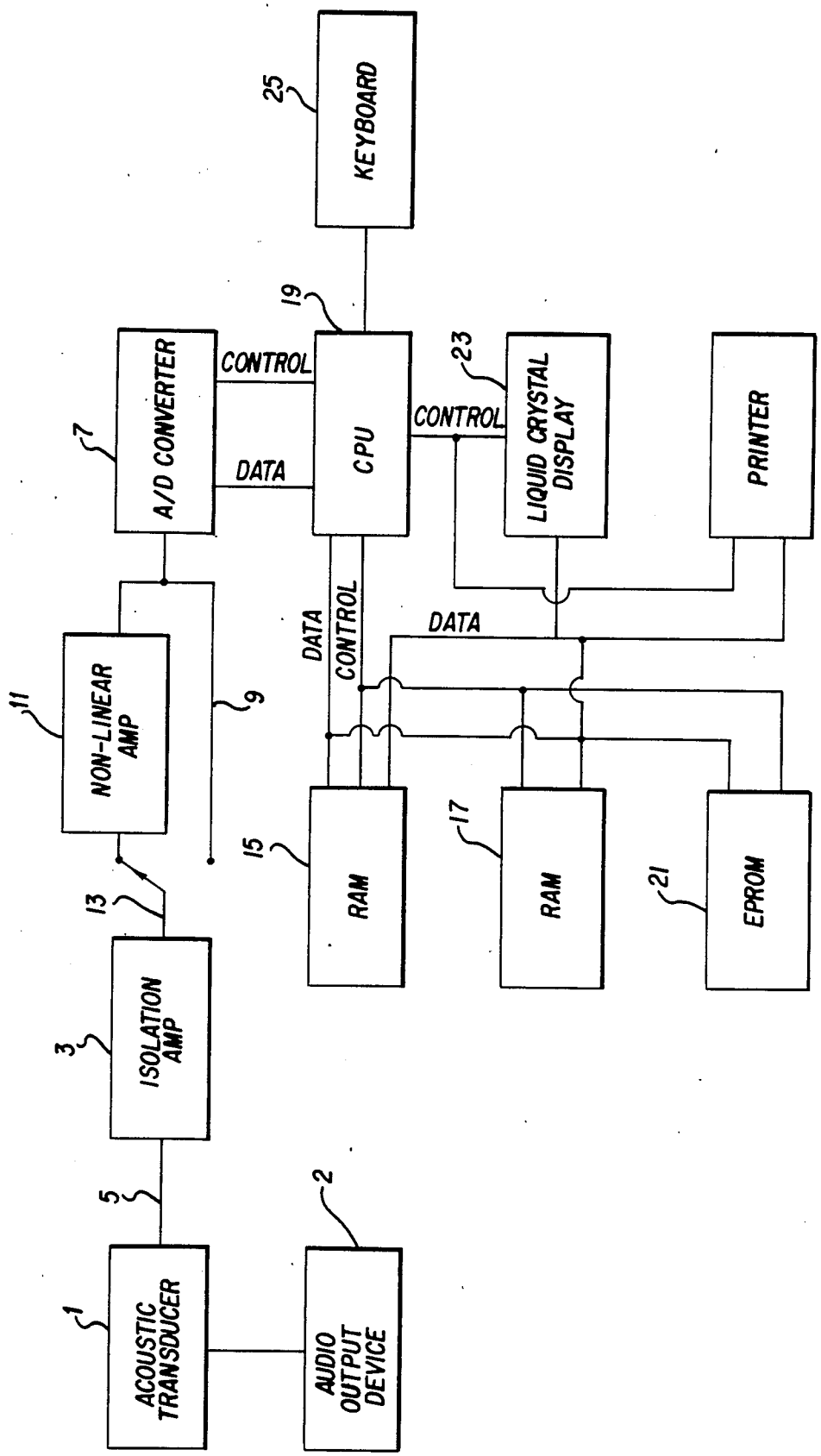
FIG. 1 is a schematic diagram of the preferred embodiment of the present invention.

Referring to the drawings, an acoustical transducer 1 detects a heartbeat and provides an analog electrical signal in accordance therewith. The acoustical transducer 1 is of the type used with electronic stethoscopes and may include built in amplifiers and filters. The output of the acoustic transducer 1 is applied to an isolation amplifier 3, which electrically isolates the acoustic transducer from the other components of the phonocardioscope. The isolation amplifier is necessary in order to prevent any possibility of electrical harm to the patient. Although the isolation amplifier isolates the transducer 1 from the other components, it also processes the output of the acoustical transducer and applies it to the phonocardioscope. The output of the acoustic transducer 1 may be coupled to the isolation amplifier 3 by a cable 5 which can be of any length desired. Alternatively transducer 1 and isolation amplifier 3 may be connected together by a connector so that the acoustic transducer is rigidly connected to the isolation amplifier.

The output of the isolation amplifier is connected to analog-to-digital converter 7, either directly through shunt 9 or through non-linear amplifier 11. Switch 13 is provided to select the coupling between the isolation amplifier and the A/D converter. The non-linear amplifier 11 has a gain which increases exponentially as a function of amplitude. Thus for low amplitude signals the gain is low and for high amplitude signals the gain is larger. The non-linear amplifier 11 enhances the S/N ratio of the analog heartbeat signal.

A/D converter 7 is a six-bit analog-to-digital converter. This is sufficient for the resolution of the liquid crystal display Y axis scale. The data output of the A/D converter, is applied to RAMs 15 and 17 where the digital heartbeat data is stored. The transfer of data from the A/D converter to the RAMs, is controlled by a microprocessor or CPU 19. The microprocessor may be for example, an Intel 8085 microprocessor. The programs for the CPU is stored in EPROM 21. Code stored in the EPROM may be erased and modified by using a UV light. A ROM can also be used instead of the EPROM.

Data stored in RAMs 15 and 17 is displayed on liquid crystal display 23. The display is controlled by CPU 19. The liquid crystal display is a 64×240 dot matrix compound graphic display such as a Hitachi LM200 Liquid Crystal Graphic Display and a suitable display driver module such as a Hitachi CB1020R Display Driver Module.

The data stored in RAMs 15 and 17 may also be printed using a dot printer 27, such as an ALPS Mod. ASG-1100. The dot printer can provide the user with a record or hard copy of the displayed data. A dot printer can be used because the data is digital.

A keyboard 25 is connected to CPU 17. The keyboard is used by an operator to select the characteristics or mode of the liquid crystal display. For example, the keyboard can be used to select the scale factor such as the display of data from 0.25 sec. or 2.0 sec., and the starting and/or resetting of the display. Furthermore, the keyboard may provide for remote operation of the display by an operator. The RAM 17 in addition to storing the output of the keyboard provides additional memory capacity such as a scratch pad and look-up table which can be used in conjunction with RAM 15.

Figure 2:
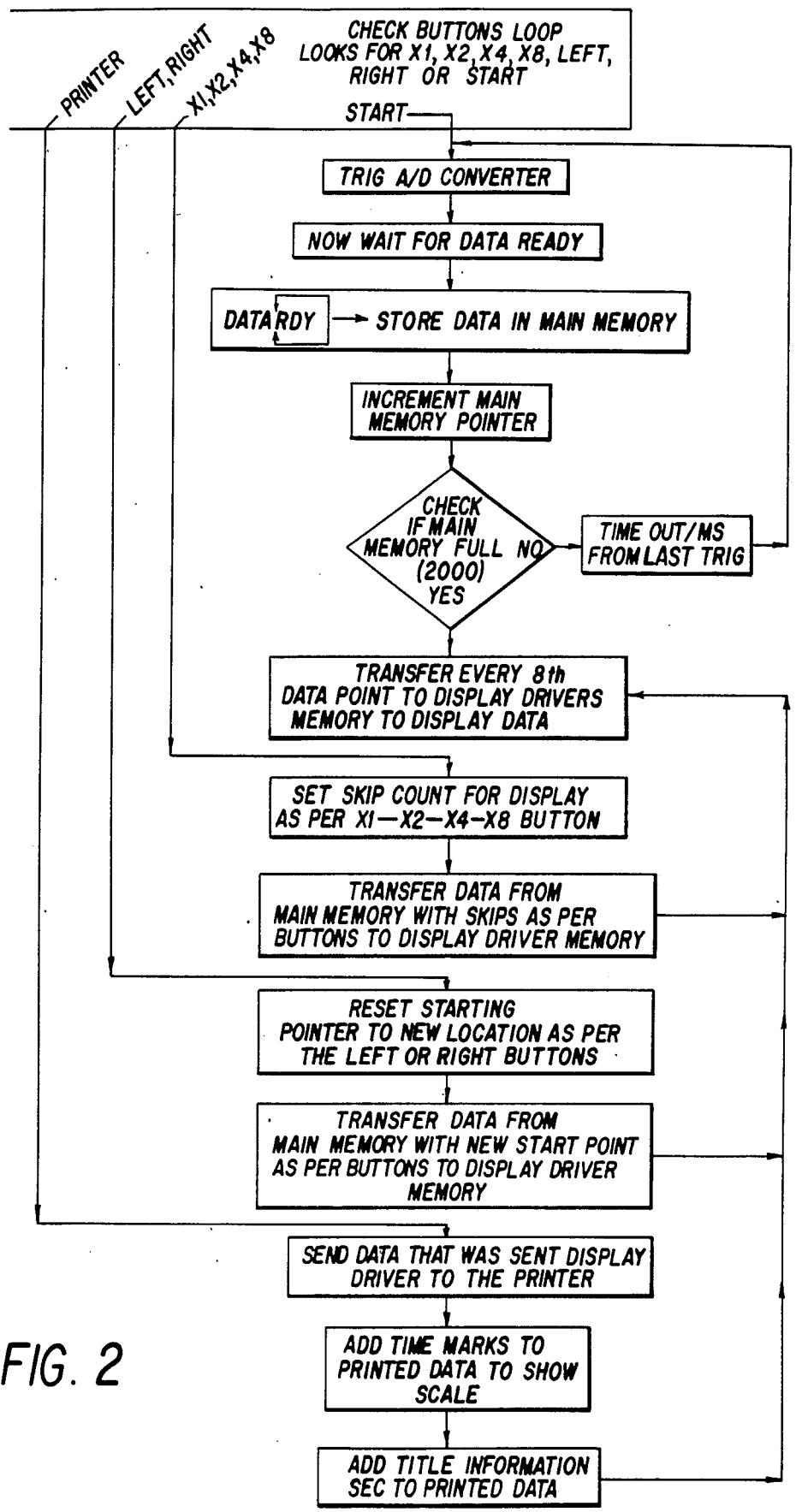
FIG. 2 is a flow chart showing the operation of the present invention.

FIG. 2 is a flow chart showing the operation of the phonocardioscope of the present invention. Prior to the displaying of data, RAM 17 receives an input from keyboard 25 which defines the expanse of the data to be displayed and the starting point of the data. The display 23 displays 256 data points. The keyboard 25 can be used to select for example, the display of every data point, every other data point, every fourth data point, or every eighth data point. In any of the displays however, 256 data points will be displayed. The operation of a start button on keyboard 25 initiates the taking of data samples from the analog input and converting it to a digital signal by the A/D converter. After the data has been converted, a read signal is sent from CPU 19 to A/D converter 7 and the data is then stored in RAM 15 through CPU 19. The program then checks the RAM 15 to determine if 2000 samples have been taken. If 2000 samples have not been taken, then the memory pointer is incremented by one and the next data sample is stored in RAM 15. After the data samples have been taken, the parameters of the display are determined by the operation of the keyboard.

If all 2000 samples have been taken, then every eighth data point starting with the first is put into the driver memory of display 23 and is then displayed.

At this point, the program then again checks the keyboard input. If one, two, four, or eight push buttons have been pressed, then appropriate data points will be skipped in the display data. Further if left or right push buttons have been pushed, then the appropriate start location will be selected.

Further, a printer may be used in conjunction with the display 23 and if the printer is operated the same data that is displayed is sent to a printer from the RAM 17. Proper time marks are sent to the printer, along with title information such as name and date labels. After display and/or printing, the program returns to start so that the operator can initiate a new display when desired.

An audio output corresponding to the analog signal from the transducer 1 is also provided by audio output device 2. The user can thus monitor the heartbeat and decide when to activate the phonocardioscope.

It is readily apparent that the above-described phonocardioscope with a liquid crystal display meets all of the objects mentioned above and also has the advantage of wide commercial utility.

The present invention may be embodied in other specific forms without departing from the spirit or essential characteristics thereof. The presently disclosed embodiments are therefore to be considered in all respects as illustrative and not restrictive, the scope of the invention being indicated by the appended claims, rather than the foregoing description, and all changes which come within the meaning and range of equivalency of the claims are, therefore, to be embraced therein.

We claim:

1. A phonocardioscope apparatus for monitoring heart functions said apparatus comprising:
   (a) acoustical transducer means for detecting the sound of heartbeats and producing an analog electrical signal in response thereto;
   (b) an analog-to-digital converter for converting said analog heartbeat signal to a digital heartbeat signal;
   (c) coupling means for coupling said transducer means to said analog-to-digital converter said coupling means including an isolation means for electrically isolating said transducer means from the other elements of said apparatus, non-linear amplifier means coupled to said isolation means for non-linearly amplifying the acoustic heartbeat signal, shunt means connected to said analog-to-digital converter in parallel with said non-linear amplifier means, and switch means for selectively applying the output of said isolation means to said non-linear amplifier means or said shunt means;
   (d) memory means coupled to said analog-to-digital converter for storing the digital heartbeat signal;
   (e) CPU means coupled to said analog-to-digital converter and to said memory means for controlling the operation thereof;
   (f) liquid crystal display means coupled to said memory means and said CPU means, wherein at least a predetermined portion of the digital heartbeat signal data stored in said memory means is displayed by said liquid crystal display means and wherein the display of the digital heartbeat signal data is controlled by said CPU means.

2. A phonocardioscope apparatus as set forth in claim 1, wherein said CPU means includes EPROM means, said EPROM means storing the programs for said CPU means.

3. A phonocardioscope apparatus as set forth in claim 1, wherein said memory means includes as least one RAM means.

4. A phonocardioscope apparatus as set forth in claim 3, including a keyboard means, coupled to said CPU means, for selecting the characteristics of the display of the heartbeat data.

5. A phonocardioscope apparatus as set forth in claim 1, wherein said CPU means includes ROM means, said ROM means storing programs for said CPU means.

6. A phonocardioscope as set forth in anyone of claims 1-4 and 5, further including printer means coupled to said memory means and said CPU means for providing a printed record of the heartbeat signal data stored in said memory means.

* * * * *